United States Patent [19]

Gold et al.

[11] 4,173,583

[45] Nov. 6, 1979

[54] DIASTEREOISOMERS OF 5-(1-HYDROXY-2-(1-METHYL-3-PHENYL-PROPYLAMINO)ETHYL)SALICYLAMIDE

[75] Inventors: Elijah H. Gold, West Orange; Wei Chang, Livingston, both of N.J.

[73] Assignee: Schering Corporation, Kenilworth, N.J.

[21] Appl. No.: 944,505

[22] Filed: Sep. 21, 1978

Related U.S. Application Data

[63] Continuation-in-part of Ser. No. 569,043, Apr. 17, 1975, abandoned.

[51] Int. Cl.$^2$ ............................................. C07C 103/26
[52] U.S. Cl. .............................. 260/559 S; 260/559 A
[58] Field of Search ......... 260/559 A, 559 S, DIG. 7, 260/DIG. 8

[56] References Cited

U.S. PATENT DOCUMENTS

| | | | |
|---|---|---|---|
| 3,644,353 | 2/1972 | Lunts et al. | 260/559 S X |
| 3,933,911 | 1/1976 | Main | 260/559 A X |
| 3,949,088 | 4/1976 | Samuelsson et al. | 260/559 A X |
| 4,000,192 | 12/1976 | Lunts et al. | 260/559 A X |
| 4,000,193 | 12/1976 | Lunts et al. | 260/559 A X |
| 4,012,444 | 3/1977 | Lunts et al. | 260/559 S |
| 4,041,075 | 8/1977 | Smith | 260/559 A X |
| 4,101,579 | 7/1978 | Hartley et al. | 260/559 A X |

FOREIGN PATENT DOCUMENTS 1266058 3/1972 United Kingdom.

OTHER PUBLICATIONS

Farmer et al., CA 77:147680v (1972).

*Primary Examiner*—Thomas Waltz
*Attorney, Agent, or Firm*—Barbara L. Cowley Renda; Mary S. King; Bruce M. Eisen

[57] ABSTRACT

Disclosed is an improved process for separating 5-[1-hydroxy-2-(1-methyl-3-phenylpropylamino)ethyl]-salicylamide into its two diastereoisomeric racemates; a process for converting either diastereoisomer into the other; and the use of one specified diastereoisomer as a superior antiarrhythmic agent.

11 Claims, No Drawings

DIASTEREOISOMERS OF 5-(1-HYDROXY-2-(1-METHYL-3-PHENYL-PROPYLAMINO)ETHYL)SALICYLAMIDE

This application is a continuation-in-part application of copending U.S. Ser. No. 569,043, filed Apr. 17, 1975, now abandoned.

The present invention relates to a process for separating and interconverting the two diastereoisomers of 5-[1-hydroxy-2-(1-methyl-3-phenylpropylamino)ethyl]salicylamide, and to the use of a specified diastereoisomer agent.

British Pat. No. 1,266,058 describes a broad series of compounds which include 5-[1-hydroxy-2-(1-methyl-3-phenylpropylamino)ethyl]salicylamide. It notes that this compound has two asymmetric centers making four optical enantiomorphs possible, and that the compound can be separated into two diastereoisomers via their benzoate salts. The patent also discloses that this series of compounds can block $\alpha$- and $\beta$-adrenergic receptors and thus may be used as hypotensive agents, and in the treatment of Raynaud's disease and angina pectoris.

Farmer, et. al., British Journal of Pharmacology, 45, 660–675 (1972), disclose that the diastereoisomeric mixture of 5-[1-hydroxy-2-(1-methyl-3-phenylpropylamino)-ethyl]salicylamide, designated AH5158, blocks both $\alpha$- and $\beta$-adrenergic receptors, and has antiarrhythmic, hypotensive and antianginal properties.

The $\beta$-adrenergic blocking activity of AH5158 reduces the tachycardia produced as a side effect of the $\alpha$-adrenergic blocking activity. Since $\alpha$- and $\beta$-blockade removes sympathetic nervous system input, there is a tendency toward cardiac depression together with a reduction of blood pressure and of coronary perfusion, all of which are undesirable in patients with compromised hearts. Accordingly, an antiarrhythmic agent with reduced adrenergic blocking activity as compared with that of AH5158 would have greater safety for such patients.

We have surprisingly discovered that one diastereoisomer of AH5158, designated herein as diastereoisomer A, has a markedly superior therapeutic index as an antiarrhythmic agent than its racemic parent. Specifically, diastereoisomer A has significantly less $\alpha$- and $\beta$-adrenergic blocking and hypotensive activity, without its antiarrhythmic activity being significantly reduced.

The method of treating arrhythmia without significant side effects of adrenergic blocking comprises administering to a warm blooded mammal an amount sufficient to treat said arrhythmia of diastereoisomer A of 5-[1-hydroxy-2-(1-methyl-3-phenylpropylamino)ethyl]salicylamide or a pharmaceutically acceptable acid addition salt thereof, substantially free of diastereoisomer B. "Treating" includes both therapeutic and prophylactic treatment, but in particular treating arrhythmia due to myocardial infarction.

Diastereoisomer A may be administered per se or in the form of its pharmaceutically acceptable acid addition salts, e.g., those formed with maleic, acetic, phthalic, succinic, lactic, tartaric, citric, malic, cinnamic, sulphonic, hydrochloric, hydrobromic, sulfuric and phosphoric acids. The salts may be prepared by the standard technique of precipitation by treatment of a solution of the free base in a suitable organic solvent with the desired acid. Further purification, if necessary, may be effected by recrystallization.

Diastereoisomer A is effective against various types of arrhythmias, e.g., atrial and ventricular. Based upon laboratory test procedures, the effective intravenous or oral dosage of diastereoisomer A against ventricular arrhythmias caused by coronary artery ligation (tachyarrhythmias following myocardial infarction), is within the range of 1 to 10 mg/kg, of mammalian body weight. Accordingly, the effective intravenous or oral dose range can be expected to be about 300 to 600 mg per 70 kg mammal. The exact dose to be administered would depend upon the age and weight of the mammal involved and the severity of the condition and would be determined by the attending diagnostician.

The compositions of the invention may be administered alone or combined with other medicinals. The method of administration may be oral, sublingual or parenteral. In any event, a suitable pharmaceutical carrier is employed, selected according to the physical properties of the active compound in the pharmaceutic composition. The carrier should not react chemically with the compound to be administered. The preparations containing the active ingredients may be in the form of tablets, capsules, solutions and the like.

As the term is used herein, "diastereoisomer A" is the one designated Isomer 1 in Example 14 of the above British Pat. No. 1,266,058 and can be characterized as the isomer whose hydrochloride has the higher melting point. We found the latter melting point to be 212°–214° C. and the hydrochloride of diastereoisomer B (designated Isomer 2) has a melting point of 175°–177° C., although said Example 14 of British Pat. No. 1,266,058 reports the melting point to be 220° C. and 174° C., respectively.

We have discovered an improved procedure for efficiently separating the two diastereoisomers. Moreover, our process also enables one diastereoisomer to be converted into the other. Our process comprises preparing a solution of 5-[1-hydroxy-2-(1-methyl-3-phenylpropylamino)ethyl]salicylamide, a suitable organic sulfonic acid and a lower alkanoic acid in a neutral solvent and separating out solid diastereoisomer B (as its sulfonate salt) leaving a mother liquor containing the remainder of diastereoisomer B and virtually all of diastereoisomer A. Then a mineral acid is added to separate out diastereoisomer A. The undesired diastereoisomer may be heated, e.g., under reflux, in dilute acid to effect interconversion (to equilibrium) and then recycled. According to the invention, racemic 5-[1-hydroxy-2-(1-methyl-3-phenylpropylamino)ethyl]salicylamide is separated into its diastereoisomers by the process which comprises:

(a) Preparing a solution of racemic 5-[1-hydroxy-2-(1-methyl-3-phenylpropylamino)ethyl]salicylamide, a suitable organic sulfonic acid and an alkanoic acid having 1 to 6 carbon atoms in a neutral solvent;

(b) separating diastereoisomer B therefrom in the form of its salt with the sulfonic acid, leaving a mother liquor containing diastereoisomer A; and (c) adding a mineral acid to the mother liquor whereby diastereoisomer A separates out as its salt with that mineral acid.

The sulfonic acid is preferably a monocyclic aromatic sulfonic acid such as a toluene-sulfonic acid. The neutral solvent is preferably an inert organic solvent.

When only one diastereoisomer is required, the unwanted diastereoisomer can advantageously be subjected to the step of (d) refluxing in dilute aqueous acid to effect at least partial equilibration; then steps (a), (b)

and (c) can be repeated. Thus, diastereoisomer B may be subjected to at least partial equilibration, and further diastereoisomer A may then be isolated by the method of steps (a), (b) and (c).

In a preferred embodiment of this process, 5-[1-hydroxy-2-(1-methyl-3-phenylpropylamino)ethyl]-salicylamide is dissolved in a $C_1$–$C_5$ alkanol, preferably isopropanol. p-Toluenesulfonic acid and acetic acid are added in approximately the same molar ratio of p-toluenesulfonic acid to acetic acid as diastereoisomer B to diastereoisomer A in 5-[1-hydroxy-2-(1-methyl-3-phenylpropylamino)ethyl]salicylamide in the racemic mixture (1:1 at the start). This causes diastereoisomer B to precipitate, which is then separated, e.g., by filtration or centrifugation. Hydrochloric acid is added to the filtrate or supernatant to precipitate diastereoisomer A. To prepare substantially all of one diastereoisomer, the undesired diastereoisomer is refluxed in dilute aqueous acid, such as hydrochloric acid, for a period of from 1 to 100 hours, preferably 48 to 96 hours, after which p-toluenesulfonic acid and acetic acid are added as before, with the desired product being isolated. The procedure may be repeated until substantially all of diastereoisomer A is converted into the other, in particular until substantially all of diastereoisomer B has been converted into diastereoisomer A.

This process may be represented by the following scheme:

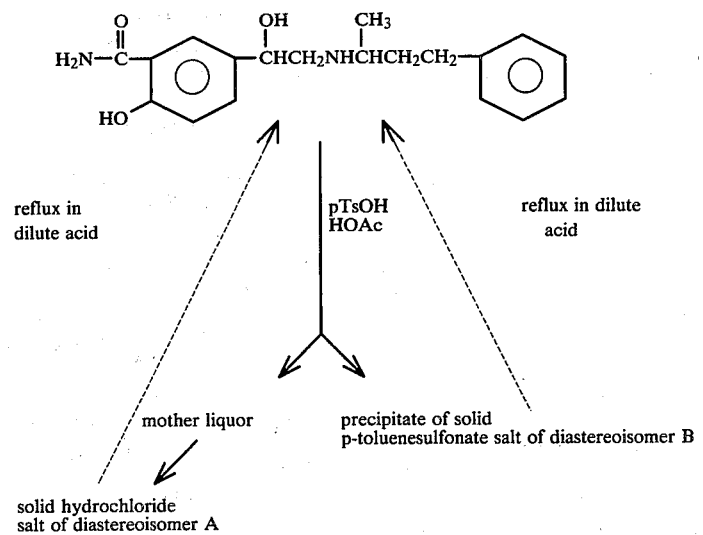

The following examples describe in detail the process of the present invention and compositions containing the compounds produced thereby. It will be apparent to those skilled in the art that many modifications, both of materials and methods, may be practiced without departing from the purpose and intent of this disclosure.

EXAMPLE 1

Separation of 5-[1-Hydroxy-2-(1-Methyl-3-Phenylpropylamino)Ethyl]Salicylamide into its Two Diastereoisomeric Components (A and B)

Add 3.4 liters of boiling isopropanol to a mixture of 532.7 g (1.625 moles) of 5-[1-hydroxy-2-(1-methyl-3-phenylpropylamino)ethyl]salicylamide (approximately 1:1 mixture of diastereoisomers A and B), 154 g (0.813 moles) of p-toluenesulfonic acid monohydrate and 48.70 g (0.813 moles) of glacial acetic acid. Reflux with stirring until total dissolution is effected and cool slowly to room temperature. Allow precipitation to take place, with occasional stirring, for about 19 hours, then filter off the crude p-toluenesulfonate salt (365 g) of diastereoisomer B, m.p. 174°–182° C. Recrystallize several times from 90% ethanol to effect purification (m.p. 186°–187° C.). Convert the p-toluenesulfonate salt of diastereoisomer B to the free base by dissolving 100 g in 400 ml of dimethylformamide and adding this solution to 7.5 liters of 0.14M aqueous sodium bicarbonate with stirring. Filter, wash with water, dry, and obtain about 55 g of diastereoisomer B, m.p. 160°–162° C. Convert diastereoisomer B to its hydrochloride salt, by dissolving the free base in ethanol and adding 1.9N ethereal hydrogen chloride. Filter, and obtain the hydrochloride salt, m.p. 175°–177° C.

To obtain diastereoisomer A as its hydrochloride salt, reduce the volume of the isopropanol solution of A (mainly as its acetate salt) to about two liters and then add 470 ml of 1.9N ethereal hydrogen chloride, while stirring and cooling. Recrystallize the resulting precipitate from 2.2 liters of 90% ethanol and then digest the resulting precipitate for 5 minutes with 2 liters of boiling ethanol. Chill and filter to obtain 174 g, m.p. 212°–214° C. (90% pure). Recrystallize twice more from ethanol, (using about 1.65 liters) to increase the purity to 98.5% (estimated by gas-liquid chromatography). Recrystallize again if higher purity is desired.

EXAMPLE 2

Conversion of Diastereoisomer B

Reflux (in a nitrogen atmosphere) 20 g of the hydrochloride salt of diastereoisomer B in 1 liter of 0.0275 N hydrochloric acid for 65 hours. Remove the solvent in vacuo, triturate with ethanol and filter off the racemic product. Remove the solvent from the filtrate and triturate the residue with acetonitrile and filter off more solid which is combined with the first crop. This racemized can now be treated as in Example 1, to obtain the diastereoisomer A. If so desired, diastereoisomer A can be racemized in an analogous manner to effect substantial conversion into diastereoisomer B.

EXAMPLE 3

Pharmaceutical Preparations

Capsules

Mix together 500 g powdered active ingredient with a sufficient quantity of microcrystalline cellulose N.F. and fill into No. 3 hard gelatin capsules so that each of 1,000 capsules contains about 500 mg of the mixture.

Tablets

Mix together 1,000 g active ingredient, 500 g lactose an 175 g corn starch and sufficient of a 2% aqueous solution of sodium hydroxyethylcellolose to produce a damp cohesive mass. Pass the damp mass through a No. 16 U.S. sieve and dry in a fluidised bed dryer at 60° C. Pass the dried granules through a No. 25 U.S. sieve and mix with 60 g dried corn starch and 15 g magnesium stearate. Compress the lubricated granules on suitable tableting press using ⅜" deep concave punches to produce 5,000 tablets each weighing about 350 mg and containing 200 mg of active.

These tablets may be film coated with suitable film forming materials such as methyl cellulose, hydroxypropylmethyl cellulose or ethyl cellulose or mixtures of these materials using standard techniques.

The tablets may also be sugar coated by the standard sugar coating techniques.

What is claimed is:

1. A process for separating racemic 5-[1-hydroxy-2-(1-methyl-3-phenylpropylamino)ethyl]salicylamide into its diastereoisomers which comprises:
   (a) preparing a solution of racemic 5-[1-hydroxy-2-(1-methyl-3-phenylpropylamino)ethyl]salicylamide, a suitable organic sulfonic acid and an alkanoic acid having 1 to 6 carbon atoms in a neutral solvent;
   (b) separating diastereoisomer B therefrom in the form of its salt with the sulfonic acid, leaving a mother liquor containing diastereoisomer A; and
   (c) adding a mineral acid to the mother liquor whereby diastereoisomer A separates out as its solid salt with that mineral acid;

said diastereoisomer A being characterized as that diastereoisomer whose hydrochloride salt has the higher melting point.

2. A process as claimed in claim 1 wherein the sulfonic acid is a monocyclic aromatic sulfonic acid.

3. A process as claimed in claim 1 wherein the sulfonic acid is p-toluenesulfonic acid.

4. A process as claimed in claim 1 wherein the alkanoic acid is acetic acid.

5. A process as claimed in claim 1 wherein the molar ratio of p-toluenesulfonic acid to acetic acid is substantially the same as the molar ratio of diasteroisomer B to diastereoisomer A in the racemate.

6. A process as claimed in claim 1 wherein the neutral solvent is an alkanol having 1 to 5 carbon atoms.

7. A process as claimed in claim 1 wherein the neutral solvent is isopropanol.

8. A process as claimed in claim 1 wherein the mineral acid is hydrochloric acid.

9. A process as claimed in claim 1 which comprises the steps of:
   (a) preparing a solution of racemic 5-[1-hydroxy-2-(1-methyl-3-phenylpropylamino)ethyl]salicylamide, p-toluenesulfonic acid and acetic acid in isopropanol;
   (b) separating diastereoisomer B therefrom in the form of its toluene-p-sulfonate salt, leaving a mother liquor containing diastereoisomer A; and
   (c) adding hydrochloric acid to the mother liquor whereby diastereoisomer A separates out as its solid hydrochloride salt.

10. A process as claimed in claim 9 wherein the molar ratio of p-toluenesulfonic acid to acetic acid is substantially the same as the molar ratio of diastereoisomer B to diastereoisomer A in the racemate.

11. A process as claimed in claim 1 including the step of:
   (d) refluxing one of the separated diastereoisomers in dilute aqueous acid to effect at least partial equilibration; and then repeating steps (a), (b) and (c).

* * * * *